United States Patent [19]
Shelton

[11] 4,083,956
[45] Apr. 11, 1978

[54] ANHYDROUS ANTIPERSPIRANT CREAMS

[75] Inventor: David Lee Shelton, Cincinnati, Ohio

[73] Assignee: The Procter & Gamble Company, Cincinnati, Ohio

[21] Appl. No.: 681,319

[22] Filed: Apr. 29, 1976

[51] Int. Cl.² .......................... A61K 7/34; A61K 7/38
[52] U.S. Cl. ........................................ 424/66; 424/68
[58] Field of Search ................................... 424/66, 47

[56] References Cited
U.S. PATENT DOCUMENTS

| | | | |
|---|---|---|---|
| 2,498,514 | 2/1950 | Van Mater | 424/66 X |
| 2,865,859 | 12/1958 | Lubowe | 424/66 X |
| 3,088,874 | 5/1963 | Geary et al. | 424/66 X |
| 3,255,082 | 6/1966 | Barton | 424/66 X |
| 3,300,387 | 1/1967 | Kole | 424/66 X |
| 3,325,367 | 6/1967 | Miechowski | 424/66 |
| 3,407,254 | 10/1968 | Siegal et al. | 424/66 |
| 3,963,833 | 6/1976 | De Salva et al. | 424/66 |

Primary Examiner—Dale R. Ore
Attorney, Agent, or Firm—George W. Allen; Douglas C. Mohl; Richard C. Witte

[57] ABSTRACT

Anhydrous antiperspirant compositions in the form of thixotropic creams. Such compositions, which contain emollients, gelling agents and antiperspirant active ingredients, are physically stable and cosmetically superior to conventional antiperspirant cream products.

11 Claims, No Drawings

ANHYDROUS ANTIPERSPIRANT CREAMS

BACKGROUND OF THE INVENTION

The present invention relates to antiperspirant compositions. Antiperspirant active is delivered to the skin by means of an anhydrous thixotropic cream vehicle containing particular concentrations of emollients and gelling agents.

Antiperspirant compositions in the form of creams are well known. Antiperspirant creams are commonly manufactured as oil/water emulsions with the antiperspirant active being dissolved in the aqueous portion of such emulsion compositions. While oil/water emulsions provide a convenient vehicle for storing and delivering antiperspirant actives, compositions of this type tend to produce an undesirable wet, cold and/or sticky sensation when they are applied to and rubbed into the skin.

The undesirable sensation produced by oil/water emulsion products can be minimized somewhat by utilizing compositions in anhydrous form. Anhydrous antiperspirant compositions can, for example, be produced in aerosol form (See Wahl; U.S. Pat. No. 3,725,540; issued Apr. 3, 1973); in semi-solid form (See Moore; U.S. Pat. No. 2,087,161; issued July 13, 1937) and in the form of a solid waxy stick (See the application of Elsnau having Ser. No. 632,128, filed Nov. 4, 1975, now U.S. Pat. No. 4,049,792, issued Sept. 20, 1977).

Anhydrous non-antiperspirant compositions in cream form are also known. An anhydrous medicament base, for example, is disclosed in Chang et al; U.S. Pat. No. 3,924,004; issued Dec. 2, 1975. Anhydrous rouge compositions are disclosed in Balsam and Sagarin; *Cosmetics Science and Technology*, 2nd. Ed., Vol. 1, Wiley-Interscience, 1972 in Chapter 11 at pgs. 355 - 358. Gelled ointment bases, emollients and polar liquids have been disclosed in Chen; U.S. Pat. No. 3,733,403; issued May 15, 1973 and in National Lead Company's Data Sheet B-18 entitled "Bentone 18-C" dated Jan. 31, 1962.

In spite of the above described prior art attempts, formulation of cream products in the form of anhydrous thixotropic gels is not accomplished without certain difficulties. Gelled compositions tend to exhibit syneresis, a bleeding or leaking of the gelled organic liquid from the gel structure or matrix. Further, such compositions may also tend to dry out or form crusts along those surfaces of the compositions which are exposed to the atmosphere.

Given the above-described problems and difficulties in providing antiperspirant products in cream form, there is clearly a continuing need for new and useful antiperspirant creams which are efficacious and which are aesthetically and cosmetically acceptable for sale as consumer products. Accordingly, it is an object of the present invention to provide anhydrous antiperspirant creams which do not impart an undesirable, cold, wet or sticky sensation when applied to the skin.

It is a further object of the present invention to provide such antiperspirant creams in the form of stable anhydrous trixotropic gels.

It is a further object of the present invention to provide such anhydrous thixotropic antiperspirant creams which exhibit minimal syneresis or bleeding of organic liquid from the thixotropic gel structure.

It is a further object of the present invention to provide such anhydrous antiperspirant creams which do not dry out or form unacceptable crusts upon prolonged exposure to the atmosphere.

It has been surprisingly discovered that the above objectives can be realized and superior antiperspirant creams provided by formulating anhydrous thixotropic creams utilizing particular amounts of certain types of emollients, suspending/thickening agents, gel promoting agents, and antiperspirant actives.

SUMMARY OF THE INVENTION

The present invention relates to substantially anhydrous antiperspirant compositions in the form of thixotropic creams resistant to syneresis. The claimed compositions comprise from about 30% to 60% by weight of a liquid organic emollient material, from about 3.0% to 9.0% by weight of an inorganic clay suspending/thickening agent, from about 1.0% to about 3.0% by weight of a gel promoting agent and from about 20.0% to about 45.0% by weight of a solid impalpable particulate astringent antiperspirant material.

The liquid organic emollient can be any non-toxic, non-irritating organic substance having a melting point of about 20° C. or lower.

The inorganic clay suspending/thickening agent is any conventional clay material suitable for forming a thixotropic cream or gel in admixture with the liquid organic emollient.

The gel promoting agent can be alkanols containing from 1 to 5 carbon atoms, acetone or propylene carbonate.

The solid impalpable particulate astringent antiperspirant material is suspended uniformly throughout the thixotropic antiperspirant composition.

DETAILED DESCRIPTION OF THE INVENTION

The substantially anhydrous antiperspirant cream compositions of the present invention essentially comprise a liquid emollient, an inorganic clay thickening-/suspending agent, a gel-promoting agent and an astringent antiperspirant material. Each of these ingredients as well as optional components and composition preparation and use are discussed in detail as follows:

Liquid Organic Emollient

The instant compositions essentially contain from about 30% to 60%, preferably from about 45% to 55%, by weight of a liquid organic emollient. An emollient is, of course, any material which can impart a soft supple character to the skin. For purposes of the instant invention, a liquid emollient is any non-toxic, non-irritating organic material which is liquid at room temperature i.e. at 20° C.

Suitable liquid organic emollients include those mineral oils, fatty acid and fatty alcohol esters and water-insoluble ethers which have melting point of 20° C. or lower. (Water-insolubility = less than about 1% by weight at 25° C.). Examples of such emollients include isopropyl myristate, isopropyl palmitate, cetyl acetate, cetyl propionate, mineral oil, di-n-butyl phthalate, diethyl sebacate, diisopropyl adipate, ethyl ethylcarbomethyl phthalate, and the condensation product of about 4 moles of propylene oxide with one mole of butyl alcohol (Fluid AP). Preferred liquid emollients include isopropyl myristate, isopropyl palmitate, mineral oil and di-n-butyl phthalate. The most preferred emollient is isopropyl myristate.

Emollients including the liquid emollients suitable for use herein are described more fully in Balsam and Sagarin, *Cosmetics Science and Technology*, 2nd. Ed., Vol. 1, Wiley-Interscience, 1972, Chapter 2, pp. 27 – 104 and in the U.S. patent application of Wilmer L. Luedders and Thomas A. Wetzel having Serial No. 571,812, filed April 25, 1975, now U.S. Pat. No. 4,045,548, issued Aug. 30, 1977. Both are incorporated herein by reference.

Clay Thickening/Suspending Agent

The instant compositions also comprise from about 3.0% to about 9.0%, preferably from about 5.0% to 7.0%, by weight of an inorganic clay thickening/suspending agent.

Clay thickening/suspending agents suitable for use in the compositions of the present invention are selected from the group consisting of montmorillonite clays and hydrophobically treated montmorillonite clays. Montmorillonite clays are those which contain the mineral montmorillonite and are characterized by having a suspending lattice. Examples of these clays include the bentonites, hectorites, and colloidal magnesium aluminum silicates.

Bentonite is colloidal, hydrated aluminum silicate obtained from montmorillonite and has the formula $Al_2O_3 4SiO_2 \cdot H_2O$. A more detailed discussion of bentonites can be found in the *Kirk-Othmer Encyclopedia of Chemical Technology*, 2nd. Ed., Vol. 3 (1964), pp. 339 – 360, published by Interscience Publishers, which is incorporated herein by reference.

Hectorite, also a montmorillonite clay, differs from bentonite in that there is almost a complete substitution of aluminum in the lattice structure of bentonite by magnesium. In addition, hectorites contain lithium and fluorine. Barasym NAH-100 is an example of a commercially available synthetic hectorite marketed by NL Industries, Inc.

The magnesium aluminum silicates are complexes of colloidal magnesium aluminum silicate richer in magnesium than aluminum. Magnesium aluminum silicates are commercially available as Veegum (R. T. Vanderbilt Co.).

Preferred suspending agents for use in the present invention are certain hydrophobically treated montmorillonite clays, e.g., hydrophobic bentonites available under the tradename of "Bentone". Bentone is prepared by reacting bentonite in a cation exchange system with an amine. Different amines are reacted to obtain a variety of Bentones, which may also differ in proportions of $SiO_2$, $MgO$ and $Al_2O_3$. Specific examples of Bentones within the scope of the present invention are Bentone 38, Bentone 34, Bentone 27, Bentone 14, and Bentone LT, all of which have a particle size of below about 5 microns and are commercially available from the NL Industries, Inc. (formally National Lead Company). Bentone 27 is the most preferred suspending/thickening agent and is described in greater detail in Technical Bulletin F-71-66 from the National Lead Company entitled "BENTONE 27" (incorporated by reference).

Use of the clay suspending/thickening agents in the present compositions is essential for the formation of thixotropic anhydrous antiperspirant creams. By utilizing clays of the particular type described and in the concentrations specified, cream compositions can be formulated which exhibit minimal undesirable syneresis and which are aesthetically and cosmetically desirable for use as commercial antiperspirant products.

Gel-Promoting Agents

Another essential component of the present invention is a gel-promoting agent used to impart the requisite gel-like consistency to the instant thixotropic antiperspirant compositions. Gel-promoting agents generally comprise from about 1.0% to 3.0% by weight of the compositions herein, preferably from about 1.5% to 2.5% by weight.

Gel-promoting agents useful herein include the $C_{1-5}$ alkanols (methanol, ethanol, propanol, butanol, pentanol), acetone and propylene carbonate. Mixtures of such gel-promoting agents i.e. specially denatured alcohol (SDA-40) can also be employed. Propylene carbonate is the most preferred gel-promoting agent.

Astringent Antiperspirant Material

The present compositions also essentially contain from about 20.0% to 45.0% by weight, preferably from about 25.0% to 40.0% by weight, of an impalpable particulate astringent antiperspirant material. Any aluminum or zirconium astringent antiperspirant salt or complex in the form of impalpable particles can be employed. Such salts and complexes are well known in the antiperspirant art.

Preferred antiperspirant actives include impalpable aluminum chlorhydroxide and aluminum hydroxybromide as well as the antiperspirant actives disclosed in the abandoned application of Raymond E. Bolich, Jr., having Ser. No. 59,690, filed July 30, 1970 and in U.S. Pat. No. 3,792,068, issued Feb. 12, 1974 to Leudders et al.

This Leudders et al patent discloses a complex of aluminum, zirconium and amino acid formed by A. Co-dissolving in water
1. one part $Al_2(OH)_{6-m}X_m$, wherein X is an anion selected from the group consisting of chloride, bromide and iodide and m is a number from about 0.8 to about 1.2;
2. *n* parts ZrY wherein Y is an anion selected from the group consisting of —O(OH)Cl and $OCl_2$, and where *n* has a value of from about 0.16 to about 1.2;
3. *p* parts neutral amino acid selected from the group consisting of glycine, dl-tryptophane, dl-β-phenylalanine, dl-valine, dl-methionine and β-alanine, and where *p* has a value of from about 0.06 to about 0.53;

B. Co-drying the resultant mixture at a temperature of from about 100° C. to about 230° C. to a moisture level of from about 0.5% to about 15% by weight; and C. Comminuting the resultant dried inorganic-organic antiperspirant complex into the form of an impalpable powder.

The preferred aluminum compound for preparation of the Leudders et al complex is aluminum chlorhydroxide of the formula $Al_2(OH)_5Cl \cdot 2H_2O$. The preferred zirconium compound for preparation of the Leudders et al complex is zirconyl hydroxychloride having the formula $ZrO(OH)Cl \cdot 3H_2O$. The preferred amino acid for preparing the Leudders et al complex is glycine of the formula $CH_2(NH_2)COOH$. (Salts of such amino acids can also be employed in such antiperspirant complexes.)

Other preferred actives for use in the present invention include mixtures of aluminum chloride and aluminum hydroxychloride.

As discussed more fully hereinafter, the astringent antiperspirant material in impalpable particulate form is dispersed throughout and suspended in the thixotropic cream compositions. Particle size of the antiperspirant active preferably ranges from about 1 to 100 microns, more preferably from about 1 to 50 microns.

Optional Components

The anhydrous antiperspirant compositions herein can contain a variety of non-essential optional ingredients suitable for rendering such compositions more aesthetically desirable. Such optional components include waxy composition application aids, anti-syneresis agents, perfumes, dyes, pigments and coloring agents.

Composition Application Aids

Highly preferred optional ingredients are those materials which enhance the ease of axillary applicability of the present antiperspirant compositions. Such composition application aids are especially useful for improving the "glide" of the present compositions where they are to be applied by means of a coated-substrate applicator such as a pad or dauber.

Composition application aids can be any organic waxy material which is "solid" at room temperature. Thus, any non-toxic, non-irritating organic wax having a melting point between greater than about 20° C. and 65° C. can be employed in the present compositions as application aids. Such organic waxy materials include fatty acids containing from about 8 to 20 carbon atoms, faty alcohols containing from about 8 to 20 carbon atoms, silicone waxes and glycerol monostearate. Especially preferred materials of this type are the $C_8$ to $C_{20}$ fatty acids and $C_8$ to $C_{20}$ fatty alcohols. The most preferred composition application aids are cetyl alcohol, stearyl alcohol, myristyl alcohol and lauryl alcohol.

If present, the composition application aids generally comprise from about 1.0% to 20.0% by weight of the composition. Preferably, such materials comprise from about 3.0% to 15.0% by weight of the composition.

It is, of course, possible to also add minor amounts (up to 3.0%, preferably less than about 1.0%) of waxy materials having melting points higher than 65° C. as composition thickeners and application aids. Such materials include waxes such as beeswax, spermaceti, carnuba, bayberry, candelilla, montan, ozokerite, ceresin, paraffin, Fischer-Tropsh waxes and microcystalline wax. Care should be taken, however, to avoid concentrations of such higher melting waxes that would destroy the thixotropic cream character of the instant compositions.

Anti-Syneresis Agents

Other highly preferred optional composition ingredients are those anti-syneresis agents which serve to further minimize and inhibit bleeding of fluid from the thixotropic antiperspirant creams of the present invention. Materials of this type include polysiloxane fluids of the formula $—[R_2SiO]—$ wherein R is $C_1 - C_4$ alkyl or phenyl and wherein the fluid has a viscosity at 25° C. of from about 1.0 to 2,000 centistokes. Preferred materials of this type are the dimethyl siloxane polymers such as SWS-03314 (Stauffer Chemical Company); UC-7207 (Union Carbide Corp.); DC-344 (Dow Corning Corporation); DC-200 (Dow Corning Corporation) and mixtures of such polymers.

If present, anti-syneresis agents comprise from about 1.0% to 30.0% by weight of the composition, preferably from about 5.0% to 20.0% by weight of the composition. Polysiloxane materials of the type described are believed to inhibit composition syneresis by strengthening the gel matrix of the cream product.

Perfumes, Dyes, Pigments and Coloring Agents

Minor ingredients such as perfumes, dyes, pigments and coloring agents can be added to the instant compositions to improve the comsumer acceptability of such products. If present, such agents generally comprise from about 0.1% to 2.0% by weight of the composition.

Composition Preparation

The compositions of the present invention are prepared by admixing the essential and optional components together in such a manner as to produce a thixotropic cream. In a preferred method of composition preparation, the emollient and optional materials soluble therein are mixed together. The clay suspending/thickening agent is then added to the liquid emollient and mixed with a suitable agitating device for several minutes to form a uniform composition. Gel-promoting and anti-syneresis agents can then be added under continuing agitation until gellation occurs. Once a thixotropic gel has formed, particulate antiperspirant actives can then be blended into the thixotropic mixture and uniformly dispersed and suspended throughout.

Various types of mixing or agitating means can be employed for preparation of the present compositions. For example, the emollient, suspending/thickening agent and gel-promoting agent can be admixed in a colloid mill or Osterizer to form the thixotropic gel matrix. Suspension of the antiperspirant active within the thixotropic gel can be accomplished with a Hobart mixer or a colloid mill. It will be recognized that the physical nature of the thixotropic creams produced can be varied by altering composition agitation time and the type of shear utilized. The skilled artisan will be able to select composition preparation means and methods suitable for providing antiperspirant creams of desired consistency and texture.

It should further be noted that the compositions of the present invention are substantially anhydrous. For purposes of the instant invention, substantially anhydrous compositions are those containing less than about 1.0% by weight free moisture. Care should be taken in preparing the instant compositions to avoid use of any materials or procedures which might introduce free moisture into the composition in excess of the substantially anhydrous level.

Composition Use

The anhydrous antiperspirant compositions of the present invention are used in the same manner as any conventional antiperspirant composition to inhibit axillary perspiration. The present compositions can be easily rubbed into the skin leaving little or no perceptible residue. Such compositions further minimize some of the conventional oil/water emulsion product shortcomings such as wetness, stickiness, coldness, etc.

The instant compositions can be easily applied by any suitable means including the use of fingers, pads, daubers, sheets, etc. Such compositions can be packaged in any suitable container including jars, packets, tubes, bottles, extruding devices, etc.

The anhydrous antiperspirant cream compositions of the present invention are illustrated by the following examples:

EXAMPLE I

An anhydrous antiperspirant composition of the following formulation is prepared:

| Component | Wt. % |
|---|---|
| Isopropyl Palmitate Emollient | 57% |
| Bentone 38 Suspending/Thickening Agent (Amine-Treated Montmorillonite Clay) | 8% |
| Methanol Gel-Promoting Agent | 3% |

-continued

| Component | Wt. % |
|---|---|
| Aluminum Chlorhydroxide Antiperspirant (Average particle size = 25 microns) | 32% |
| | 100% |

Such a composition is prepared by mixing the isopropyl palmitate and Bentone 38 in an Osterizer to form a thickened liquid of uniform consistency. Methanol is then added under agitation until gellation is observed. The composition is transferred to a Hobart mixer where the antiperspirant active is blended into the gelled mixture.

The composition so produced is an effective anhydrous antiperspirant composition in the form of a stable thixotropic cream. The composition exhibits minimal syneresis and does not provide an undesirable wet, sticky or cold sensation when applied and rubbed into the skin.

Compositions of substantially similar physical/cosmetic character and antiperspirant effectiveness are realized when in the Example I composition the isopropyl palmitate emollient is replaced with an equivalent amount of isopropyl myristate, cetyl acetate, cetyl propionate, mineral oil, di-n-butyl phthalate, diethyl sebacate, diisopropyl adipate, ethyl ethylcarbomethyl phthalate or Fluid AP (Butyl alcohol condensed with about 4 moles of propylene oxide).

Compositions of substantially similar physical/cosmetic character and antiperspirant effectiveness are realized when in the Example I composition the Bentone 38 suspending/thickening agent is replaced with an equivalent amount of Bentone 27, Bentone 34, Bentone 14, Bentone LT (All amine treated montmorillonites available from NL Industries, Inc.), Veegum (Magnesium aluminum silicate available from R. T. Vanderbilt Co.) or Barasym NAH-100 (Synthetic hectorite available from NL Industries, Inc.)

EXAMPLE II

An anhydrous antiperspirant composition of the following formulation is prepared:

| Component | Wt. % |
|---|---|
| Isopropyl Myristate Emollient | 32% |
| Bentone 38 Suspending/Thickening Agent (Amine-Treated Montmorillonite Clay) | 7% |
| SDA-40* Gel-Promoting Agent | 3% |
| ZAG** Antiperspirant Active | 47% |
| SWS-03314 Siloxane *** Antisyneresis Agent | 10% |
| Perfume | 1% |
| | 100% |

*Specially Denatured Alcohol
**Zirconium hydroxychloride/aluminum chlorohydroxide/glycine complex prepared in accordance with Luedders et al, U.S. Patent 3,792,068, issued February 12, 1974. Average particle size = 25 microns.
***Dimethyl siloxane polymer of viscosity 2.3 cs at 25° C. marketed by Stauffer Chemical Company.

Such a composition is prepared in a manner similar to that described in Example I. The composition so produced is an effective anhydrous antiperspirant composition in the form of a stable thixotropic cream. The composition exhibits minimal syneresis and does not provide an undesirable wet, sticky or cold sensation when applied and rubbed into the skin.

Compositions of substantially similar physical/cosmetic character and antiperspirant effectiveness are realized when in the Example II composition the SDA-40 gel-promoting agent is replaced with an equivalent amount of ethanol, propanol, butanol, pentanol, acetone, propylene carbonate or mixtures of these materials.

Compositions of substantially similar physical/cosmetic character and antiperspirant effectiveness are realized when in the Example II composition the SWS-03314 antisyneresis agent is replaced with an equivalent amount of the following dimethyl polysiloxanes: UC-7207 (Union Carbide Corporation); DC-344 (Dow Corning Corporation); DC-200 (Dow Corning Corporation) or mixtures of these polysiloxanes.

EXAMPLE III

An anhydrous antiperspirant composition of the following formulation is prepared:

| Component | Wt. % |
|---|---|
| Isopropyl Myristate Emollient | 55.00% |
| Bentone 27 Suspending/Thickening Agent (Amine-treated Montmorillonite Clay) | 6.10% |
| Propylene Carbonate Gel-Promoting Agent | 2.00% |
| ZAG* Antiperspirant Complex | 31.40% |
| Cetyl Alcohol Application Aid | 4.75% |
| Perfume | 0.75% |
| | 100.00% |

* Zirconium hydroxychloride/Aluminum chlorhydroxide/Glycine complex prepared in accordance with Luedders et al, U.S. Pat. 3,792,068; issued Feb. 12, 1974. Average particle size = 25 microns.

Such a composition is prepared in a manner similar to that described in Example I. The IPM/Bentone/Propylene Carbonate mixture is, however, heated to a temperature of about 50° C. prior to the addition of the cetyl alcohol and ZAG to facilitate dissolution of the cetyl alcohol in the cream formulation. The composition so produced is an effective anhydrous antiperspirant composition in the form of a stable thixotropic cream. The composition exhibits minimal syneresis and does not provide an undesirable wet, sticky or cold sensation when applied and rubbed into the skin.

Compositions of substantially similar physical/cosmetic character and antiperspirant effectiveness are realized when in the Example III composition the cetyl alcohol application aid is replaced with an equivalent amount of stearyl alcohol, myristyl alcohol, lauryl alcohol or mixtures thereof.

Compositions slightly thicker than the Example III composition are realized when such a composition additionally contains minor amounts (0.9% of a higher melting wax such as beeswax, spermaceti, carnuba, bayberry, candelilla, montan, ozokerite, ceresin or paraffin.

What is claimed is:

1. A substantially anhydrous antiperspirant composition in the form of a cream resistant to syneresis, said composition comprising:

A. from about 30.0% to 60.0% by weight of a liquid organic emollient material;

B. from about 3.0% to 9.0% by weight of an inorganic clay suspending/thickening agent suitable for forming a thixotropic cream in admixture with said emollient;

C. from about 1.0% to 3.0% by weight of a gel promoting agent selected from the group consisting of an alkanol containing from 1 to 5 carbon atoms, acetone, propylene carbonate and mixtures thereof; and D. from about 20.0% to 45.0% by weight of a solid impalpable particulate astringent antiperspirant material suspended throughout said composition.

2. A composition in accordance with claim 1 wherein:
A. the emollient comprises from about 45% to 55% by weight of the composition, has a melting point of about 20° C. or less and is selected from the group consisting of mineral oil, a fatty acid ester and a fatty alcohol ester, and a water-insoluble ether;
B. the suspending/thickening agent comprises from about 5.0% to 7.0% by weight of the composition and is selected from the group consisting of montmorillonite clay and hydrophobically treated montmorillonite clay;
C. the gel-promoting agent comprises from about 1.5% to 2.5% by weight of the composition; and
D. the astringent antiperspirant material comprises from about 25% to 40% by weight of the composition and is selected from the group consisting of
   i. aluminum chlorhydroxide,
   ii. aluminum hydroxybromide,
   iii. mixtures of aluminum chlorhydroxide and aluminum chloride, and
   iv. antiperspirant complexes formed by
      a. co-dissolving in water
         1. one part $Al_2(OH)_{6-m}X_m$, wherein X is an anion selected from the group consisting of chloride, bromide and iodide and $m$ is a number from about 0.8 to about 1.2;
         2. $n$ parts ZrY wherein Y is an anion selected from the group consisting of —O(OH)Cl and $OCl_2$, and where $n$ has a value of from about 0.16 to abour 1.2;
         3. $p$ parts neutral amino acid selected from the group consisting of glycine, dl-tryptophane, dl-$\beta$-phenylalanine, dl-valine, dl-methionine and $\beta$-alanine, and where $p$ has a value of from about 0.06 to about 0.53; and
      b. co-drying the resultant mixture at a temperature of from about 100° C. to about 230° C. to a moisture level of from about 0.5% to about 15% by weight.

3. A composition in accordance with claim 2 wherein
A. the emollient is selected from the group consisting of isopropyl myristate, isopropyl palmitate, mineral oil and di-n-butyl phthalate; and
B. the astringent antiperspirant material is selected from the group consisting of aluminum chlorhydroxide, aluminum hydroxybromide, mixtures of aluminum chlorhydroxide and aluminum chloride and complexes formed from zirconium hydroxychloride, aluminum chlorhydroxide and glycine.

4. A composition in accordance with claim 3 wherein the emollient is isopropyl myristate.

5. A composition in accordance with claim 3 wherein the gel-promoting agent is propylene carbonate.

6. A composition in accordance with claim 3 wherein the astringent antiperspirant is selected from the group consisting of complexes formed from zirconium hydroxychloride, aluminum chlorhydroxide and glycine.

7. A composition in accordance with claim 3 wherein
A. the emollient is isopropyl myristate;
B. the gel-promoting agent is propylene carbonate; and
C. the astringent antiperspirant is selected from the group consisting of complexes formed from zirconium hydroxychloride, aluminum chlorhydroxide and glycine.

8. A composition in accordance with claim 3 which additionally contains from about 1.0% to 30.0% by weight of an anti-syneresis agent which is a polysiloxane fluid of the formula —$[R_2SiO]$— wherein R is an alkyl containing one to four carbon atoms, and phenyl and wherein said polysiloxane fluid has a viscosity of 25° C. of from about 1.0 to 2000 centistokes.

9. A composition in accordance with claim 3 which additionally contains from about 1.0% to 20.0% by weight of a composition application aid selected from the group consisting of a fatty acid containing from about 8 to 20 carbon atoms, a fatty alcohol containing from about 8 to 20 carbon atoms, a silicone wax and glycerol monostearate, said application aid having a melting point between greater than about 20° C. and 65° C.

10. A composition in accordance with claim 9 wherein the composition application aid is selected from the group consisting of cetyl alcohol, stearyl alcohol, myristyl alcohol and lauryl alcohol.

11. A composition in accordance with claim 10 wherein
A. the emollient is isopropyl myristate;
B. the gel-promoting agent is propylene carbonate;
C. the astringent antiperspirant is selected from the group consisting of aluminum chlorhydroxide, aluminum hydroxybromide, mixtures of aluminum chlorhydroxide and aluminum chloride and complexes formed from zirconium hydroxychloride, aluminum chlorhydroxide and glycine; and
D. the application aid is cetyl alcohol.

* * * * *